(12) United States Patent
Zajaczkowski

(10) Patent No.: US 7,347,845 B2
(45) Date of Patent: Mar. 25, 2008

(54) DISPOSABLE ABSORBENT ARTICLE HAVING TENSION INDICATORS

(75) Inventor: Peter Zajaczkowski, Media, PA (US)

(73) Assignee: SCA Hygiene Products AB, Gothenburg (SE)

( * ) Notice: Subject to any disclaimer, the term of this patent is extended or adjusted under 35 U.S.C. 154(b) by 315 days.

(21) Appl. No.: 10/904,849

(22) Filed: Dec. 1, 2004

(65) Prior Publication Data

US 2005/0119633 A1    Jun. 2, 2005

Related U.S. Application Data

(60) Provisional application No. 60/526,097, filed on Dec. 2, 2003.

(51) Int. Cl.
A61F 13/15 (2006.01)
A61F 5/00 (2006.01)
A61F 5/24 (2006.01)

(52) U.S. Cl. ............ 604/385.01; 604/386; 604/387; 604/389; 604/391; 604/392; 602/19; 128/96.1; 128/99.1

(58) Field of Classification Search ........... 604/385.01, 604/385.03, 385.04, 386, 387, 389, 391, 604/392, 394; 602/19; 128/96.1, 99.1
See application file for complete search history.

(56) References Cited

U.S. PATENT DOCUMENTS 3,309,257 A    3/1967  Borack et al.
3,361,609 A    1/1968  Borack et al.
3,613,679 A   10/1971  Bijou
4,598,003 A *  7/1986  Renholts ............... 428/40.7
4,964,858 A * 10/1990  Livny ................. 604/385.21
5,040,525 A *  8/1991  Georgijevic ............ 602/23
5,618,264 A *  4/1997  Vasquez ................ 602/24
6,152,893 A   11/2000  Pigg et al.
6,171,274 B1 * 1/2001  Nafpliotis ............. 602/75
7,074,204 B2 * 7/2006  Fujii et al. ............ 602/75
7,162,441 B2 * 1/2007  Nabarro .................. 705/26

FOREIGN PATENT DOCUMENTS

JP         1064823         3/1989
JP         2001106984      4/2001
WO          96/31175 A1   10/1996
WO       WO 98/51247 A1 * 11/1998
WO         03/022730 A1    3/2003

* cited by examiner

*Primary Examiner*—Tatyana Zalukaeva
*Assistant Examiner*—Michael G Bogart
(74) *Attorney, Agent, or Firm*—Buchanan Ingersoll & Rooney PC

(57) ABSTRACT

A disposable absorbent article having a front part, a rear part, a crotch part extending between the front and rear part, and fasteners for fastening the side portions of the front and rear parts together in an overlapping relationship in order to give the absorbent article a pants-like configuration, the overlap between the side portions of the respective front and rear part being adjustable. At least one of the side portions of the front or rear parts have at least one tension indicator.

14 Claims, 3 Drawing Sheets

DISPOSABLE ABSORBENT ARTICLE HAVING TENSION INDICATORS

CROSS-REFERENCE TO RELATED APPLICATIONS

The present application claims the benefit of U.S. Provisional Application Ser. No. 60/526,097, filed on Dec. 2, 2003.

TECHNICAL FIELD

The present invention relates to a disposable absorbent article having a front part, a rear part and a crotch part extending between the front and rear part.

BACKGROUND OF THE INVENTION

In order to obtain good fluid containment in a disposable absorbent article, such as an open type diaper, a pant diaper or an incontinence protector, a reasonably tight fit on the wearer is necessary. However, if the fit is overly tight, this can result in excess pressure on the skin of the wearer and lead to red marking or even skin abrasion. For persons with sensitive skin, like elderly persons, the consequences of an overly tight fit can be particularly severe because the skin may not regain its original shape or heal quickly. Articles of the type mentioned in the introduction are applied on the wearer by a caretaker or the wearer himself and the fit obtained is thus dependent on the person applying the article. There is thus a need for providing means for ensuring that the person applying the article will not tension the waistline of the article to such an extent that skin irritation will occur. There is also a need for indicating an appropriate tensioning in the leg elastics present in most articles of the above mentioned types. The fit of such articles is also dependent upon the right size for the wearer being chosen and, thus, there is a need for means for indicating the tension in various parts of such articles, for example in the hip areas of pant diapers.

OBJECTS AND SUMMARY

Objectives of the present invention are to prevent the person applying an absorbent article from applying too much tension to the waistline of the article and also to indicate if the article applied is of an appropriate size for the wearer in question.

One embodiment of the present invention is a disposable absorbent article having a front part, a rear part, and a crotch part extending between the front and rear part, wherein the article comprises at least one tension indicator. By such an indicator it can be ensured that the article will have a properly tight fit so that good fluid containment can be obtained without risking skin irritation. By an embodiment of the present invention it is also possible to indicate if a sufficiently tight fit is obtained.

In a preferred embodiment the article comprises fasteners for fastening the side portions of the front and rear parts together in an overlapping relationship in order to give the absorbent article a pants-like configuration, the overlap between the side portions of the respective front and rear part being adjustable, the longitudinal direction of the article runs from the rear to the front part, wherein at least one of the side portions of the front or rear parts comprise at least one tension indicator.

In an embodiment, the article can preferably comprise elastic elements along leg openings and at least one tension indicator can be disposed adjacent to at least one of said leg openings in order to indicate if the leg elastics are overly tight or loose.

A tension indicator can be disposed visually on the outside of the article in at least one side part thereof and be placed in a region between a free end of said front or rear part and a leg opening. Such an embodiment is especially convenient for pant diapers in order to verify that a correct size of the article is used.

In a preferred embodiment the tension indicator comprises a strip of plastic material that changes its visual appearance when a certain tension is applied thereto. Said plastic material is opaque until a certain tension is reached and then becomes transparent or vice versa. Alternatively, an underlying color appears when said plastic material becomes transparent.

Preferably, in an embodiment, the article comprises tension indicators of two different types, wherewith one of said indicator types indicate that a minimum tension level is reached and the other that a maximum tension level is reached.

In a preferred embodiment, said strip of plastic material is attached to an outside of the article only in the opposite lateral ends of the strip and said strip of plastic material comprises a fold between its lateral ends.

In a further embodiment at least one portion of the rear or front part of the article comprises an outer sheet of a material which visual appearance changes when a certain tension is reached in the material.

An embodiment of the invention also relates to a tension indicator comprising a strip of plastic material that changes its visual appearance when a certain tension is applied thereto.

BRIEF DESCRIPTION OF THE DRAWINGS

The invention will now be described with reference to the enclosed Figures, of which.

DETAILED DESCRIPTION OF PREFERRED EMBODIMENTS

Figure 1:
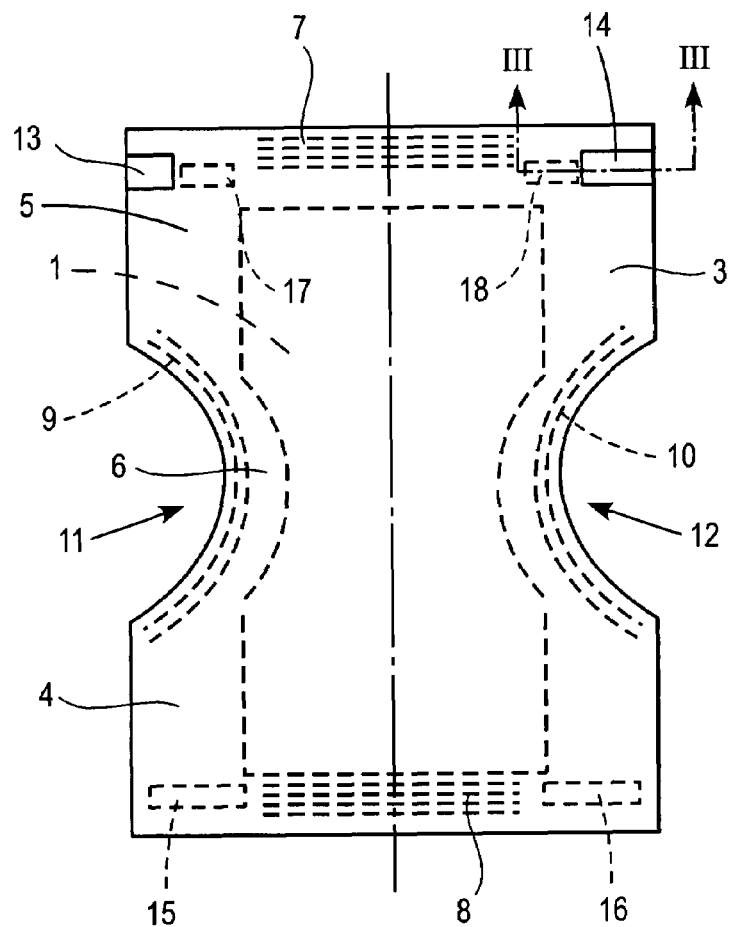
FIG. 1 shows a schematic planar view of a disposable absorbent article according to a first preferred embodiment of the invention with the inside of the article turned toward the viewer.
Figure 2:
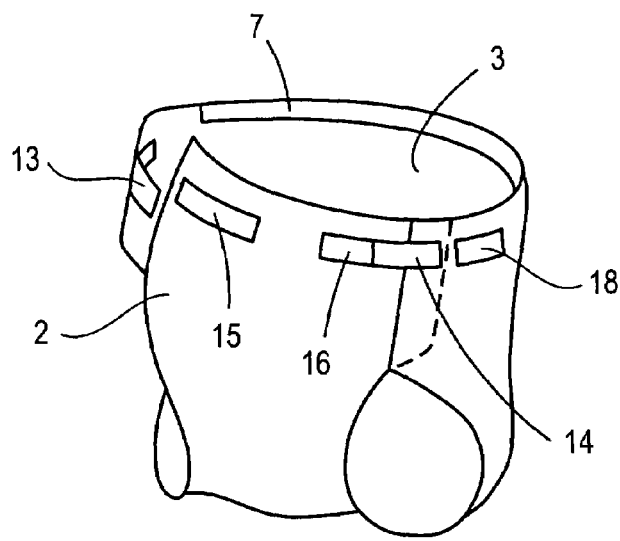
FIG. 2 shows a perspective view of the article of FIG. 1 in an almost applied state with one pair of co-operating side portions of the front and rear parts fastened to each other.
Figure 3:
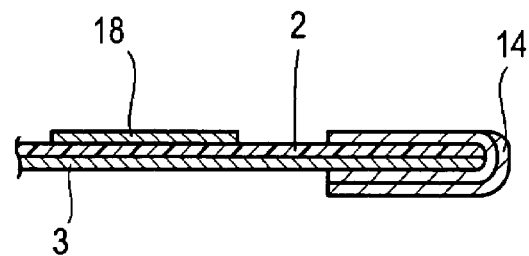
FIG. 3 shows a sectional view along line III-III in FIG. 1.

In FIGS. 1-3 a first preferred embodiment of an incontinence protector, i.e. a diaper for use by adults, is shown. As is conventional for such articles, said article comprises an absorbent body 1 enclosed between an outer liquid impermeable casing sheet 2 and an inner liquid permeable casing sheet 3. The article has an hour-glass shape with a front part 4, a rear part 5 and a crotch part 6 extending between the front and rear part. The casing sheets 2,3 are attached to each other in those portions that extend outside the absorbent body 1.

This embodiment of the article also comprises waist elastics in the form of several elastic threads 7,8 provided at the waistline of the front and rear parts, respectively, in the central parts thereof and attached to the casing sheets 2,3 in a pre-tensioned state. Pre-tensioned elastic threads 9,10 are also provided along the respective leg opening 11,12 of the article. Instead of elastic threads for the waist and/or the leg elastics it is of course possible to use elastic bands or bands of heat-shrinkable material, which shrink and obtain elastic properties after heat treatment. In FIG. 1, the article is shown with the elastics in a pre-tensioned state, i.e. without the gathering of casing material that will occur when the elastic threads are allowed to relax. The elastic threads 7-10 are disposed between the casing sheets 2,3 but it is of course possible to dispose the elastic elements on the outside or the inside of the article, i.e. on the outer sheet 2 or the inner sheet 3.

Furthermore, this embodiment of the article comprises fasteners for giving the article a pants-like configuration when applied on a wearer, as is schematically shown in FIG. 2. In the shown embodiment, the fasteners consist of tape tabs 13,14 co-operating with elongated strips 15,16 of a plastic material to which the tape tabs can be releasably attached and refastened several times, as is known in the art. Instead of tape tabs, mechanical fasteners, for example of the hook and loop type, can be used. It is to be noted that the fasteners are preferably of a type admitting adjustment of the length of the waistline so that a proper fit of the article can be obtained for wearers having different sizes and body shapes. In FIG. 2, the article is shown with tape tab 14 fastened to strip 16. As can be understood, the amount of possible overlapping between the respective pairs of side portions of the front and rear parts is determined by the length of the strips 15,16. In the disclosed embodiment the tape tabs 13,14 are disposed on the side portions of the rear part and the strips of plastic material are disposed on the side portions of the front part. It is of course possible, but not preferred, to place the tape tabs on the side portions of the front part and the strips of plastic material on the side portions of the rear part.

The material in the outer casing sheet 2 may be polyethylene or any other materials known to be used as outer casing sheet in absorbent articles. Thus, the outer casing sheet can comprise several layers laminated to each other and may for aesthetic reasons have a fabric-like layer on its outside, i.e. the side distal from the wearer of the article. The outer casing layer is, as mentioned earlier, liquid impermeable but can preferably be permeable for air and vapor.

The inner liquid permeable casing sheet 3 may be made of nonwoven material comprising fibers of polyethylene, polypropylene, polyester or mixtures thereof. Viscose fibers may also be used. It can also comprise of a perforated plastic sheet. All types of materials known to be used as inner casing sheets in disposable absorbent can be used in an article according to the present invention.

The absorbent body 1 may contain cellulose fluff pulp with or without an admixture of particles and the like of so-called superabsorbent material and/or thermoplastic melt fibers. The absorbent body may also comprise several layers of absorbent material. Layers of nonwovens or the like for improving the liquid-acquisition properties of the absorbent body and layers for improving the liquid distribution may also be provided. All types of absorbent bodies known to be used in absorbent articles may be used in an article according to the invention.

In order to make use of the good fluid containment properties of today's disposable absorbent articles, such as diapers and incontinence protectors, it is preferred that the article be properly fitted on the wearer. This means that when the article has been applied on a wearer, the waistline of the article will exert a pressure on the body of the wearer. If such pressure is too small, the article will probably leak, and if the pressure is too high, the skin of the wearer will be irritated or damaged. It has been found by the present inventor that the tension in the waistline should exceed 1 N in order to ensure a proper fluid containment and that if the tension in the waistline exceeds 8 N, damage to the skin is likely to be caused. However, the tension obtained in the waistline of the article depends on the degree of overlapping of the side portions made by the person applying the article on a wearer. In order to help such a person estimate how tight the article should be fitted on the wearer, the article according to the present invention is provided with tension indicators, such as the tension indicators 17,18 shown in FIGS. 1-3.

Tension indicators 17,18 comprise strips of plastic material which change their visual appearance when a certain tension is reached in the material. Examples of such plastic materials are unplasticized polyvinyl chloride, polyvinyl chloride-polyvinyl acetate copolymers, changing colors when subjected to cold flow deformation. In an embodiment of the invention the thickness and material in the strips 17,18 are chosen in such a manner that a visual change, a whitening, is obtained when the tension in the side portion reaches a value between the lowest value for ensuring a good fit of the article and the value causing risk for damage of the skin, preferably beyond the lower limit, if possible. The value chosen is preferably lower than the value causing risk for skin irritation or damage.

The strips 17,18 are attached to the respective side portion of the rear part 5 by any suitable means, such as glue or weld joins. In the disclosed embodiment the strips are attached to casing sheet 2 along their whole length but it is feasible to attach the strip to casing sheet 2 only at their opposed lateral ends.

When the article according to the embodiment shown in FIGS. 1-3 is applied to a wearer, the side portions of the front and rear parts are first attached to each other with an overlap on one side of the article, in the example shown in FIG. 2, the right side of the article when viewed from the front by attaching the tab 14 to the strip 16. Since the waistline of the article remains open after this measure, no appreciable tensioning of the waistline is obtained. It is first when the side portions of the front and rear parts opposite to the already attached side portions, are attached to each other with the help of fastener elements 13 and 15 that the waistline must be tensioned in order to attain a tight fit of the article. The person applying the article in the way indicated in FIG. 2 grips the tab 13 or the side portion to the left in FIG. 2 and pulls this portion in over the corresponding side portion of the front part of the article in an overlapping relationship. The greater overlap, the higher tension in the side portions. When the tension indicator 17 whitens, an appropriate overlap has been reached and the tape tab 13 is then attached to the plastic strip 15. By the provision of the tension indicator 17 it is thus very easy for a user to determine when an appropriate tension is applied.

From the foregoing description it is clear that it is enough to provide one of the side portions with a tension indicator. However, if only indicator 18 was present on the article according to FIG. 2 and the article was applied in the way described above, the person applying the article would have to study the indicator 18 on the opposite side portion to the portion last applied, when determining the appropriate overlap. This might be inconvenient and for this reason it is preferred that both of the side portions of the rear part are provided with a tension indicator.

Instead of separate strips 17,18, the tabs 13,14 or the side portions of the rear part 5 can be constructed to serve as tension indicators.

Figure 4:
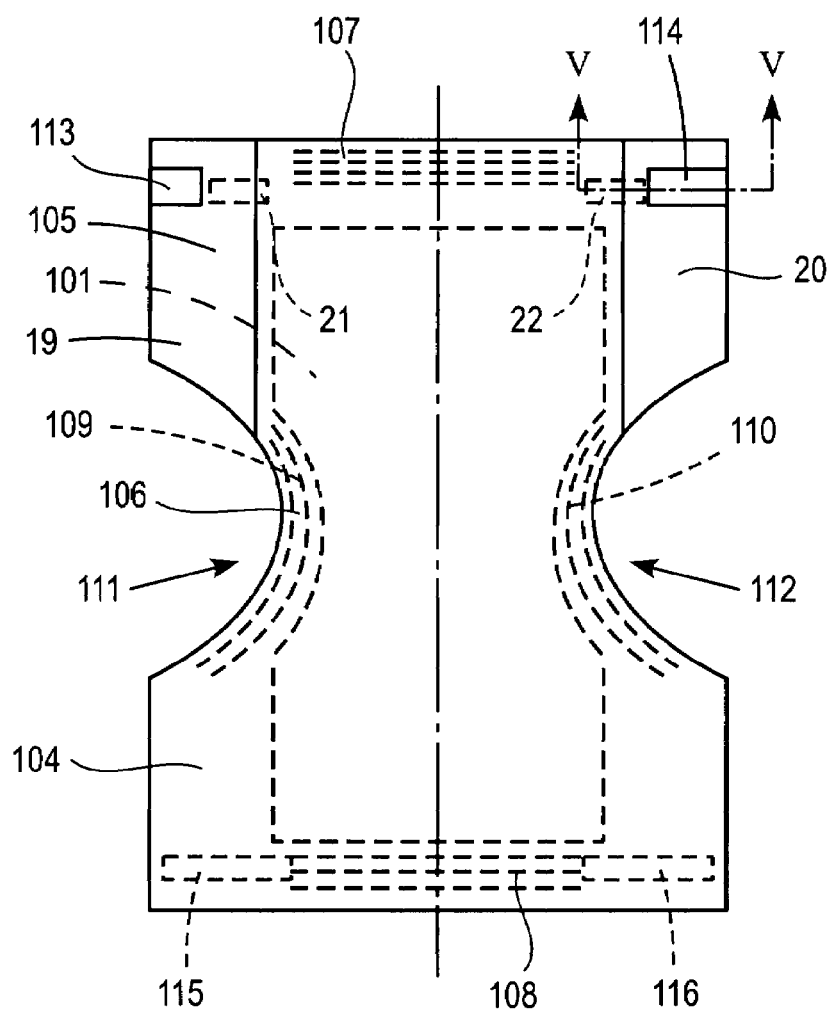
FIG. 4 shows a view similar to FIG. 1 of an article according to a second preferred embodiment of the invention.
Figure 5:
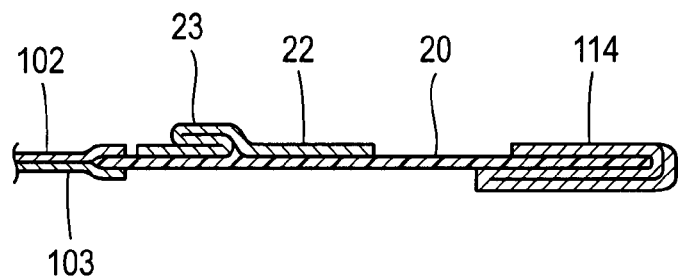
FIG. 5 shows a sectional view along line V-V in FIG. 4.

In FIG. 4 and 5, an article according to a second embodiment of the invention is shown in views corresponding to FIGS. 1 and 3, respectively. The article according to this embodiment differs from the article according to FIGS. 1-3 in that the side portions of the rear part are of elastic material, such as elastic nonwoven or the like, and constitute side panels 19, 20 attached to the casing sheets 102,103. The components of the article according to the second embodiment similar to corresponding components of the article according to the first embodiment shown in FIGS. 1-3 are given the same reference numerals in FIGS. 4 and 5 with the addition of 100. The reason for providing the article with elastic side panels 19,20 is to improve comfort and the overall fit of the article. When such an article is applied to a wearer the side panels will be elongated in a lateral direction. The materials used for tension indicators can normally not follow the elongation desired for the side panels without rupture. The tension indicators 21, 22 according to the second embodiment are therefore attached to the outer side of the side panels 19,20 in a folded condition with only the lateral ends thereof attached to the panel, as can be seen in FIG. 5. This means that in the start of the lateral elongation of the panels, no tension will be introduced in the tension indicators, the elongation of the panel 20 leading to an out-folding of the fold 23 of tension indicator 22. The lateral length of the fold 23 may be chosen so that the lowest value for ensuring a good fit of the article is reached in the side panels when the tension indicator 22 is totally unfolded. The tension at which the visual appearance of the tension will occur may then be chosen near the value causing risk for damage of the skin. In the second embodiment, according to FIGS. 4 and 5, the tension indicators 21,22 are a combination of two different tension indicators, one in which the unfolding of the tension indicator visually tells the reader that a certain tension is reached, and the other being the color change in the material, for example whitening due to cold flow deformation.

Figure 6:
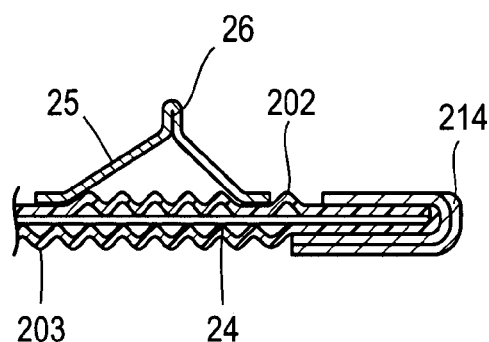
FIG. 6 shows a sectional view similar to FIG. 3 of an article according to a third preferred embodiment of the invention.

Instead of providing separate side panels of elastic material, the side portions of the rear part can be elasticized by providing pre-tensioned elastic threads between the casing sheets, said threads being attached to one or both of the casing sheets. Such side portions are present in a third embodiment of an article according to the invention, a side portion of such an article is shown in FIG. 6 in a view similar to FIG. 3, after the pre-tensioned threads has been able to relax after manufacture. The components of the article according to the third embodiment similar to corresponding components of the article according to the first embodiment shown in FIGS. 1-3 are given the same reference numerals in FIG. 6 with the addition of 200. When the means holding the elastic threads in a pre-tensioned state during manufacture are removed, said threads strive to resume their initial length, i.e. to shorten and thereby recover to a tension free state. The recovery of the elastic threads lead to a gathering of the casing sheets 202, 203 attached thereto, as is evident from FIG. 6. A tension indicator 25 attached in its lateral ends to the outer casing sheet 202 during manufacture, i.e. with the elastic threads in a pre-tensioned state, will also be gathered so that a fold occurs between its ends. In order to make use of the elasticity of the elastic threads in the side portions, some gathering of the casing sheets 202,203 shall remain in the applied condition of the article. In order for the tension indicator 25 to be subjected to tension when some gathering of the casing sheets remains, the tension indicator must be shortened after its gathering due to the recovery of the elastic threads. In the embodiment shown in FIG. 6, such a shortening is accomplished by affixing parts of the sides facing each other in the fold, for example by a glue or weld join 26 as is schematically indicated in FIG. 6. Thereafter, the indicator may be folded to a neat configuration similar to the fold 23 of the second embodiment disclosed in FIG. 5.

Figure 7:
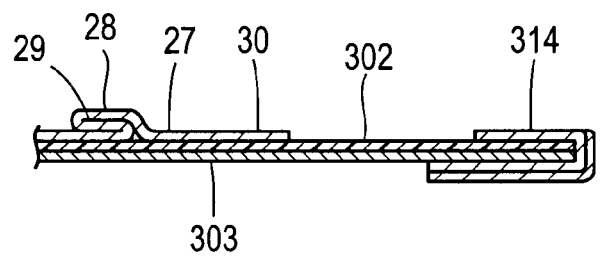
FIG. 7 shows a sectional view similar to FIG. 3 of an article according to a fourth preferred embodiment of the invention.

A fourth embodiment of an article according to the invention is shown in FIG. 7. The components of the article according to the fourth embodiment similar to corresponding components of the article according to the first embodiment shown in FIGS. 1-3 are given the same reference numerals in FIG. 7 with the addition of 300. The only difference between the first and fourth embodiment is the construction of the tension indicator. The tension indicator 27 of the fourth embodiment is releasable and refastenable in relation to the casing sheet 302, for example by being attached thereto by a suitable adhesive. The attachment is however strong enough to resist the maximum tension the tension indicator will be subjected to. Furthermore, the tension indicator 27 contains a fold 28, the sides of the indicator facing each other in the fold being attached to each other by a join 29 being of the same type as the join attaching the tension indicator to casing sheet 302. The tension indicator 27 may also have an end portion 30 unattached to casing sheet 302 in order to facilitate release of the tension indicator. By such a construction it is possible to readjust an article after a first adjustment leading to a first visual change of the indicator, the first visual change occurring in end part of the indicator turned away from the fastener 314. When a readjustment is to be done, the user grips the free end 30, unfolds fold 28 and attach the unfolded indicator to casing sheet 302 in a stretched state, the unfolded part of the fold constituting a new indicating section of the tension indicator 27. In a variation the end of the indicator opposite to end 30 might be more firmly attached to casing sheet 302 than the rest of the indicator 27. It is of course possible to provide the tension indicator with more than one fold 28 if more than one readjustment is needed.

The visual change of the material can of course be other than the appearance of a color or the unfolding of a fold. For example, an opaque indicator can turn transparent when a certain tension therein is reached. In such a case it would be preferable for the indicator to have a color other than the underlying material, obtained by, for example, coloring the indicator or the underlying material. It is also possible to use rupture of a material as a visual indication. The indicator can be a laminate of a strip of rupturing material and a strip of elastic material having a different color than the rupturing material. Such a laminate construction can also be used for the other types of indicators mentioned above.

An overly or insufficiently tight fit of absorbent articles of the above mentioned types can also result from applying articles of a too small or a too large size for the wearer in question. It is therefore appropriate to provide tension indicators on said articles in order to indicate if an appropriate size of the article is chosen. Such indicators can be placed on other parts of the article, for example adjacent to the leg elastics. For a pant diaper a tension indicator can suitably be provided in one or both of the hip regions of the diaper.

Preferably, tension indicators for indicating too low tension as well as too high tension are provided. It is also possible to construct the whole backsheet from a material that changes its visual appearance when the tension in the material is overly high. It is preferable to also provide such a backsheet with other types of tension indicators indicating if sufficient tension is obtained in sensible regions of the backsheet, such as in the leg elastics and in the side portions of the article.

The described embodiments can of course be modified within the scope of the invention. For example, the article can be a diaper for children instead of a diaper for adults. It is also possible to provide indicators parts of the article outside the waist region. The tension indicator need not be separate from the casing sheets but a weakened portion of an outer casing sheet can be used as tension indicator. More than one indicator, each indicator indicating a different tension in the waist region, can be used. Furthermore, the article can have different configuration than disclosed. For example the absorbent body can have a rectangular shape and the article can lack waist elastics. The invention shall therefore only be limited by the content of the enclosed claims and equivalents thereof.

What is claimed is:

1. A disposable absorbent article comprising a front part, a rear part and a crotch part extending between the front and rear part, wherein the article comprises at least one tension indicator, wherein the tension indicator comprises a strip of plastic material that changes its transparency when a certain tension is applied thereto.

2. The article according to claim 1, wherein the article comprises fasteners for fastening side portions of the front and rear parts together in an overlapping relationship in order to give the absorbent article a pants-like configuration, the overlap between the side portions of the respective front and rear part being adjustable, the longitudinal direction of the article runs from the rear to the front part, wherein the at least one tension indicator is on one of the side portions of the front or rear parts.

3. The article according to claim 1, wherein the article comprises elastic elements along leg openings and the at least one tension indicator is disposed adjacent to at least one of said leg openings.

4. The article according to claim 1, wherein the tension indicator is disposed visually on the outside of the article in at least one side part thereof and is placed in a region between a free end of said front or rear part and a leg opening.

5. The article according to claim 1, wherein said plastic material is transparent until a certain tension is reached and then becomes opaque.

6. The article according to claim 1, wherein said plastic material is opaque until a certain tension is reached and then becomes transparent.

7. The article according to claim 6, wherein an underlying color appears when said plastic material becomes transparent.

8. The article according to claim 1, wherein the article comprises tension indicators of two different types, wherewith one of said indicator types indicate that a minimum tension level is reached and the other that a maximum tension level is reached.

9. The article according to claim 1, wherein said strip of plastic material is attached to an outside of the article only in opposite lateral ends of the strip.

10. A disposable absorbent article comprising a front part, a rear part and a crotch part extending between the front and rear part, wherein the article comprises at least one tension indicator, wherein the tension indicator comprises a strip of plastic material, wherein said strip of plastic material is attached to an outside of the article only in opposite lateral ends of the strip, wherein said strip of plastic material comprises a fold of material with at least two fold lines between its lateral ends.

11. The article according to claim 1, wherein at least one side portion of the rear or front part of the article comprises an outer sheet of a material which transparency changes when a certain tension is reached in the material.

12. A tension indicator for a disposable absorbent article comprising a strip of plastic material that changes its transparency when a certain tension is applied thereto.

13. A disposable absorbent article comprising a front part, a rear part and a crotch part extending between the front and rear part, wherein the article comprises at least one tension indicator, wherein the tension indicator comprises a strip of plastic material that changes its hue when a certain tension is applied thereto.

14. A disposable absorbent article comprising a front part, a rear part and a crotch part extending between the front and rear part, wherein the article comprises at least one tension indicator, wherein the tension indicator comprises a laminate of a strip of material adapted to rupture at a certain tension and a strip of elastic material having a different color than the rupture material, wherein the elastic material is exposed by the rupturing of the rupture material.

* * * * *